US009928827B1

(12) United States Patent
El-Kady et al.

(10) Patent No.: US 9,928,827 B1
(45) Date of Patent: Mar. 27, 2018

(54) CHIP-SCALE PHONON-BASED QUANTUM DEVICE

(71) Applicant: Sandia Corporation, Albuquerque, NM (US)

(72) Inventors: Ihab Fathy El-Kady, Albuquerque, NM (US); Edward S. Bielejec, Albuquerque, NM (US); Charles M. Reinke, Albuquerque, NM (US); Susan M. Clark, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 280 days.

(21) Appl. No.: 15/060,434

(22) Filed: Mar. 3, 2016

Related U.S. Application Data

(60) Provisional application No. 62/128,443, filed on Mar. 4, 2015.

(51) Int. Cl.
*G06N 99/00* (2010.01)
*G10K 15/04* (2006.01)

(52) U.S. Cl.
CPC .......... *G10K 15/04* (2013.01); *G06N 99/002* (2013.01)

(58) Field of Classification Search
CPC ..... H01L 49/006; G06N 99/002; G10K 15/04
See application file for complete search history.

(56) References Cited

U.S. PATENT DOCUMENTS

| 7,836,566 B1 | 11/2010 | Olsson et al. |
| 8,508,370 B1 | 8/2013 | El-Kady et al. |
| 2014/0326902 A1* | 11/2014 | Tahan ................... H01L 49/006 250/493.1 |

OTHER PUBLICATIONS

Saeedi, K. et al., "Room-Temperature Quantum Bit Storage Exceeding 39 Minutes Using Ionized Donors in Silicon-28" Science, 2013, pp. 830-833, vol. 342.
Ruskov, R. et al., "On-Chip Cavity Quantum Phonodynamics With an Acceptor Qubit in Silicon", Pysical Review B, 2013, article 064308, vol. 88.
Soykal, O. O. et al., "Sound-Based Analogue of Cavity Quantum Electrodynamic in Silicon", Physical Review Letters, 2011, article 235502, vol. 107.
Schenkel, T. et al., "Solid State Quantum Computer Development in Silicon with Single Ion Implantation", Journal of Applied Physics, 2003, pp. 7017-7024, vol. 94.
Li, J. et al., "Ion-Beam Sculpting at Nanometre Length Scales", Nature, 2001, pp. 166-169, vol. 412.
Olsson, R. H. et al., "Microfabricated VHF Acoustic Crystals and Waveguides", Sensors and Actuators A, 2008, pp. 87-93, vol. 145-146.

(Continued)

*Primary Examiner* — Hovhannes Baghdasaryan
(74) *Attorney, Agent, or Firm* — Martin I. Finston

(57) ABSTRACT

A quantum device includes a phononic crystal defined on a semiconductor substrate. Phononic cavities are defined in the phononic crystal, wherein each phononic cavity contains an implanted acceptor atom. Phononic waveguides are defined in the phononic crystal, wherein each waveguide is coupled to at least one phononic cavity. At least some phononic waveguides are arranged to provide coupling between phononic cavities and ultrasonic transducers. At least some phononic waveguides are arranged to provide coupling between different phononic cavities.

10 Claims, 10 Drawing Sheets

(56) References Cited

OTHER PUBLICATIONS

Hopkins, P. E. et al., "Reduction in the Thermal Conductivity of Single Crystalline Silicon by Phononic Crystal Patterning", Nano Letters, 2011, pp. 107-112, vol. 11.

Goettler, D. F. et al., "Realization of a 33 GHz Phononic Crystal Fabricated in Freestanding Membrane", AIP Advances, 2011, article 042001, vol. 1.

El-Kady, I. et al., "Phonon Manipulation with Phononic Crystals" SAND2012-0127 (2012).

Olsson, R. H. et al., "Research on Micro-Sized Acoustic Bandgap Structures", SAND2010-0044 (2010).

Schenkel, T. et al., "Solid State Quantum Computer Development in Silicon with Single Ion Implantation", Journal of Applied Physics, 2003, pp. 7017-7024, vol. 11.

Soliman, Y.M. et al., "Phononic Crystals Operating in the Gigahertz Range with Extremly Wide Band Gaps", Applied Physics Letters, 2010, article 193502, vol. 97.

Stein, D.M. et al., "Feedback-controlled Ion Beam Sculpting Apparatus", Review of Scientific Instruments, 2004, pp. 900-905, vol. 75.

Eichenfield, M. et al., "Design, Fabrication, and Measurement of RF IDTs for Efficient Coupling to Wavelength-Scale Structures in Thin Piezoelectric Films", Joint UFFC< EFTF and PFM Symposium IEEE, 2013, Appendix A1.

El-Kady, I. et al., "Chip Scale Phonon-Based Scalable Quantum Computing", SPOE NDE, Mar. 10, 2015, San Diego, CA.

Olsson, R. H. et al., "Microfabricated Phononic Crystal Devices and Applications", Measurement Science and Technology, 2009, article 012002, vol. 20.

El-Kady, E. et al., "Phononic Band-Gap Crystals for Radio Frequency Communications", Applied Physics Letters, 2008, article 233504, vol. 92.

Clark, S. et al., "Phonon-Based Scalable Quantum Computing on Chip", APS March Meeting, 2014, Denver, CO.

Eichenfield, M. et al., "Designing Microwave Frequency Electromehanical Transducers for Efficient Acoustic Actuation of Nanoscale Structures", 2012, Sandia LDRD Day, Santa Fe, NM.

* cited by examiner

CHIP-SCALE PHONON-BASED QUANTUM DEVICE

This application claims the benefit of U.S. Provisional Application Ser. No. 62/128,443, which was filed on Mar. 4, 2015. The entirety of the abovesaid Application Ser. No. 62/128,443 is hereby incorporated herein by reference.

STATEMENT OF GOVERNMENT INTEREST

This invention was made with Government support under Contract No. DE-AC04-94AL85000 awarded by the U.S. Department of Energy. The Government has certain rights in the invention.

FIELD OF THE INVENTION

The invention relates to methods and apparatus for creating and maintaining entangled quantum-mechanical states of atoms or ions for quantum computing and other kinds of quantum information processing.

ART BACKGROUND

Quantum information processing promises to perform some significant tasks far more efficiently than can be accomplished classically. Important examples of possible applications include quantum computation, quantum simulation, and quantum communication (collectively, "quantum information processing"). Physical systems of various kinds are under consideration for quantum information processing. Trapped atomic systems, which may be ions or neutral atoms, constitute one promising type of physical system.

A common characteristic of physical environments for quantum information processing is that they can support qubits and that they can maintain the qubits for a coherence time that is long enough to permit quantum computations to take place.

A qubit is a physical system that has two quantum mechanical states, and that can exist in a superposition of those two states. The possibility of superposition of states is an essential feature of quantum information processing. The two states of a qubit are often represented in Dirac notation by the symbols 10> and 1>, respectively.

Individual qubits are defined in the trapped atomic system by isolating two quantized energy levels of the atomic configuration. Different states can include configurations of various properties of the atomic electron and nucleus such as electron orbit, electron spin, and nuclear spin. Controlled atomic transitions can be performed by applying excitation pulses at suitable resonant energies. Although these pulses are typically pulses of electromagnetic radiation, it has also been proposed to use mechanical energy, in the form of phononic pulses, to induce transitions in some systems.

Another important feature in many aspects of quantum information processing is entanglement. Two particles are said to be entangled if the quantum state of one cannot be described without reference to the other. Stated more formally, a system is entangled if its quantum state cannot be factored as a product of the individual states of its constituent particles. As a consequence of entanglement, the outcome of an experiment that collapses the quantum state of a first particle to produce an observable measurement can be correlated with the outcome of a similar experiment performed on a second particle that is entangled with the first, even if at the time of measurement the particles are separated by a macroscopic distance that precludes mutual interaction.

Quantum computing fundamentally depends on the ability to concurrently entangle and control a large number of qubits. However, the technical barriers to scaling quantum computing to large numbers of entangled qubits are high. For example, inhomogeneity has been an impediment in systems based on quantum dots, spectral crowding has been an impediment in systems that rely on proximity-based entanglement in ions, weak interactions have been an impediment in systems using neutral atoms, and extreme requirements for fabrication tolerances have been an impediment in systems based on silicon vacancies and on SQUIDs.

Accordingly, there is a need for new physical systems for quantum information processing that are scalable.

SUMMARY OF THE INVENTION

We have developed a qubit system with individually addressable qubits that we believe to be inherently scalable. It is a solid-state system based on the coupling of a phonon with an acceptor impurity in a high-Q mechanical resonant cavity.

Others have experimentally confirmed that in cavities with strong mutual phononic coupling, transitions between hyperfine atomic levels can be induced by mechanical vibrations. However, for applications in quantum computing the phonon coupling must be weak enough to permit the acceptor atoms to relax and exchange phonons with acceptor atoms in other cavities.

We have found that by engineering the resonant cavities appropriately, it is possible to achieve a significant enhancement of the phonon emission rate through the Purcell Effect. More specifically, the phonon emission rate is enhanced, at appropriate coupling strengths, by a multiplicative factor F, referred to as the "Purcell factor", which in terms of the modal volume V, cavity quality factor Q, and phononic wavelength $\lambda/n$, is given by $$= \frac{3}{4\pi^2}\left(\frac{\lambda}{n}\right)^2 \frac{Q}{V}.$$

The Purcell factor was first computed for the rate of spontaneous emission of photons in the context of cavity quantum electrodynamics. However, the same results apply by analogy, mutatis mutandis, to the spontaneous emission of phonons.

The enhanced emission rate due to the Purcell effect is helpful in ensuring that the device can make computations at sufficient speed. Weak coupling, however, is desirable to assure that the states remain coupled into the same cavity mode. Hence for a given system there is an optimum coupling strength that best balances this tradeoff.

Ions implanted in silicon for the purpose of storing quantum states have already been shown to exhibit extremely long coherence times. K. Saeedi et al., "Room-Temperature Quantum Bit Storage Exceeding 39 Minutes Using Ionized Donors in Silicon-28," *Science* 342 (15 Nov. 2013) 830-833 reported the implantation of a donor ion in isotopically pure silicon. The isotopic purity was required because donors exhibit spin-coupling to the substrate material, which can lead to rapid decoherence.

The need for isotopic purity is a disadvantage of the Saeedi approach because isotopically pure silicon is very expensive. We believe that because acceptors exhibit much weaker substrate spin-coupling, our acceptor-based approach can achieve relatively long coherence times even without isotopic purity.

Accordingly, the invention in one aspect is a quantum device in which a phononic crystal is defined on a semiconductor substrate. In embodiments, a plurality of phononic cavities is defined in the phononic crystal, and each of the phononic cavities contains an implanted acceptor atom whose internal states serve as the physical qubits for the system. The qubits can communicate with each other through a phononic bus, defined by phononic waveguides in the phononic crystal. Qubit control and readout is also mediated by phonons, which are coupled into and out of the system by ultrasonic transducers.

DETAILED DESCRIPTION

Figure 1:
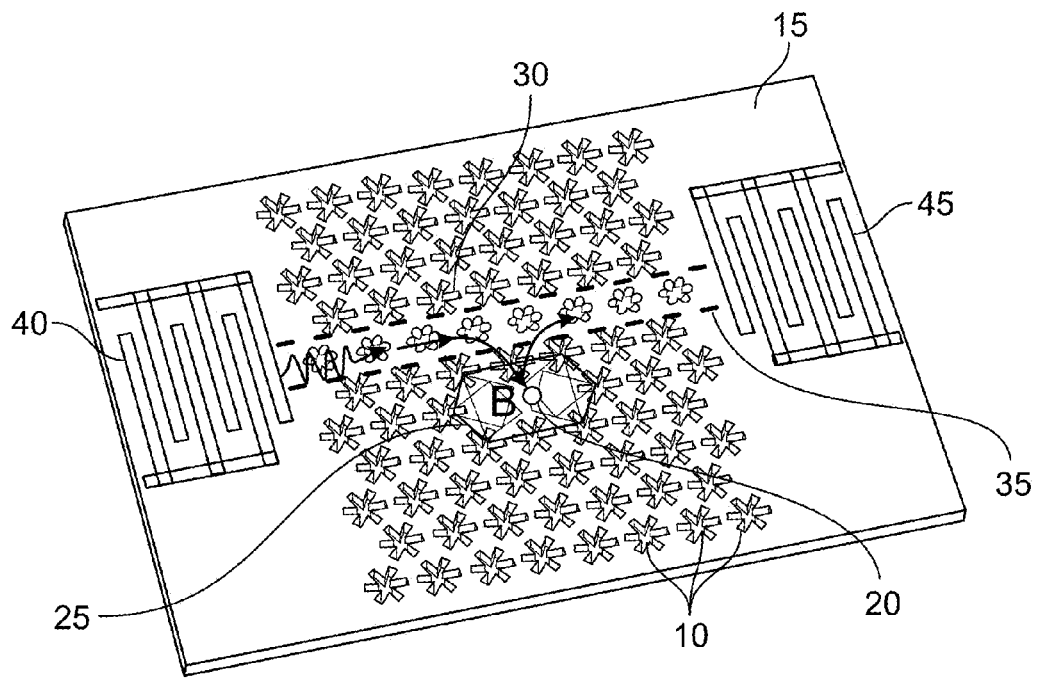
FIG. 1 is schematic perspective view, looking down, of an example device that illustrates certain principles of the present invention.

Acceptor qubits implanted in silicon have been studied before. In particular, R. Ruskov and C. Tahan, "On-chip cavity quantum phonodynamics with an acceptor qubit in silicon," *Physical Review B* 88 (2013) article 064308, pages 1-7 (hereinafter, Ruskov 2013) reports on a qubit similar to the one we describe here. Both Ruskov 2013 and Ö. O. Soykal et al., "Sound-Based Analogue of Cavity Quantum Electrodynamics in Silicon," *Physical Review Letters* 107 (28 Nov. 2011), article 235502, pages 1-4 (hereinafter, Soykal 2011) describe extensions of the quantum electrodynamic treatment of atomic optical transitions in cavities to analogous systems in which phonons rather than photons are coupled to the atomic states.

One central idea that is developed in Ruskov 2013 and Soykal 2011 is that the well-known Jaynes-Cummings Hamiltonian, which was originally derived to describe optical transitions of a two-level atom interacting with a quantized mode of an optical cavity, can be extended so that it also applies to systems that couple phonons to atomic states.

The entirety of Ruskov 2013 and the entirety of Soykal 2011 are hereby incorporated herein by reference. Ruskov 2013 and Soykal 2011 are useful references for understanding the physical mechanisms that underlie the present invention.

Our physical system is a silicon-based phononic crystal (PnC) in which isolated acceptor atoms are implanted. An illustrative example of an acceptor element is boron. Other acceptor elements that could be useful in this context are aluminum, gallium, and indium.

Silicon is not the only possible membrane material on which to base the phononic crystal, although silicon is especially advantageous because of ease of fabrication and because even natural silicon contains a low number of nuclear spins, which leads to favorable decoherence properties. However, other possible materials are not excluded. Possible alternative materials include, e.g., silicon carbide and isotopically purified zinc selenide.

A PnC is an artificial structure in which the mechanical impedance of a body varies periodically due to the introduction of holes (or other mechanical perturbations) into the body. This periodic variation results in rich phonon dispersion that can in certain instances exhibit a phononic bandgap, i.e., a frequency range where no phonons are allowed to propagate. By selectively introducing and engineering defects in the (typically two-dimensional) periodic lattice, it is possible to create intra-gap phononic states. More specifically, localized defects can create resonant cavities, and line defects can create phononic waveguides.

In implementations, the PnC is a silicon wafer perforated with a regular two-dimensional lattice of holes. The defects are created by varying the size and shape of the holes. (In some cases, selected holes may be omitted so that the substrate is imperforate at the hole lattice site.) By selecting the design parameters, waveguides can be designed to have designated transition bands, for example narrow transition bands that encompass and are approximately centered on the cavity resonance.

Also by selecting the design parameters, the cavities can be designed to have a designated resonance that lies within the phononic bandgap. Because of the extreme narrowness of the atomic transitions, the cavity resonances will inherently be wider than the atomic resonances. This is desirable because it leads to tolerances for various types of fabrication error. It is also important for the modal volume of the phonon resonance within the cavity to be large enough to tolerate straggle, i.e. error in the location of the implanted acceptor atom.

FIG. 1 provides an example in which a lattice of holes 10 perforates silicon wafer 15. An isolated boron atom 20 is implanted within a cavity-type defect region 25. A line-defect region 30 defines a phononic waveguide 35. An interdigitated aluminum nitride transducer 40 provides acoustic input to waveguide 35, and a similar transducer 45 provides output from the waveguide.

Figure 2:
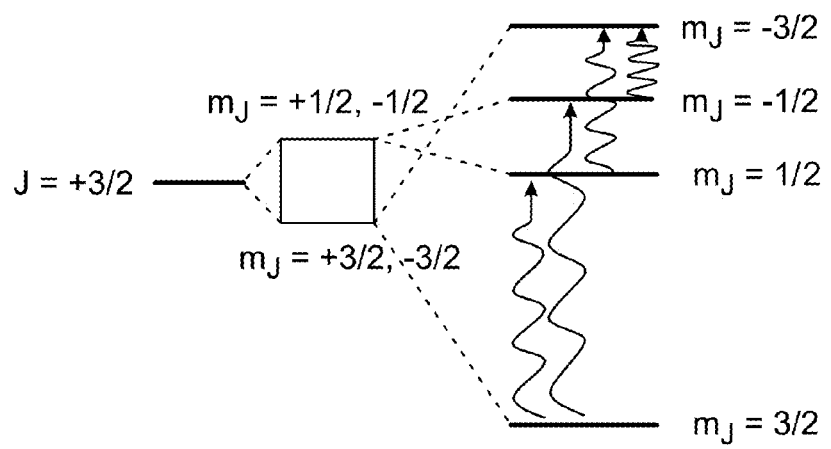
FIG. 2 is an energy-level diagram of an acceptor boron atom in a physical system of the kind described here.

With reference to FIG. 2, we will now discuss the pertinent electronic fine structure of an acceptor boron atom that has been selectively placed in a Si-based phononic crystal (PnC) cavity. (In the following discussion, the terms "atom" and "ion" will be used interchangeably when referring to an implanted atomic species.)

As those skilled in the art will appreciate, a boron atom that is substituted for a silicon atom in the crystal lattice contributes only three electrons, i.e. one fewer than silicon's four electrons. Alternatively stated, boron contributes five holes, which is one greater than silicon's four holes. At high temperatures, the extra hole has enough energy that it tends to break free from the boron atom and propagate freely in the lattice, leaving behind a negatively charged atom. At low temperatures, however, a hole can be weakly bound to the boron atom, cancelling its net charge. The weakly bound hole occupies a hydrogenic orbit. The atomic states of interest here are the hydrogen-like states of the weakly bound hole.

A DC magnetic field is used to split the atomic states of the boron atom via the Zeeman effect, so as to create an energy spacing that is resonant with the PnC cavity. More specifically, the cavity resonance in the phononic crystal should be wide enough to encompass the Zeeman splitting of the two active levels in the atomic spin manifold. Optimally, the cavity resonance would exactly coincide with the atomic resonance. However, exact coincidence is not necessary. This is important because it relaxes constraints on fabrication error and makes it a practical possibility to fabricate an operative device.

As seen in the figure, the small background strain induced in the wafer by the implanted boron atom splits the J=+3/2 state into a pair of degenerate Kramers doublets with $m_J=\pm 1/2$ and $m_J=\pm 3/2$, respectively. The Zeeman field, which has a typical strength of 1-3 T, removes the degeneracies. It splits the lower doublet into a high-energy $m_J=-3/2$ level and a low-energy $m_J=+3/2$ level. It splits the upper doublet into a higher-energy $m_J=-1/2$ level and a lower-energy $m_J=+1/2$ level.

The wiggly arrows in the figure indicate the allowed transitions, which all occur in the gigahertz frequency range. Using the notation $|m_J\rangle$, the allowed transitions are: $|3/2\rangle \rightarrow |1/2\rangle$, $|3/2\rangle \rightarrow |-1/2\rangle$, $|1/2\rangle \rightarrow |-3/2\rangle$, and $|-1/2\rangle \rightarrow |-3/2\rangle$.

The theory of cavity quantum electrodynamics (QED) provides a formalism for calculating the coupling of photons to atomic states through spin-orbit coupling. Analogously, spin-orbit coupling also enables phonons to be strongly coupled with the atomic states. These phonons can both probe and manipulate the internal atomic states that serve as the quantum memories in our system.

We can make our modal volume small, for example about one cubic micrometer, which is on the order of one wavelength cubed. For such volumes, our calculations show that for resonance at a frequency of about 5 GHz, and with cooling in a $^3$He cryostat to 270 mK, a Purcell enhancement factor P of up to about 1000 can be achieved with a relatively modest Q factor of about 5000.

Figure 3:
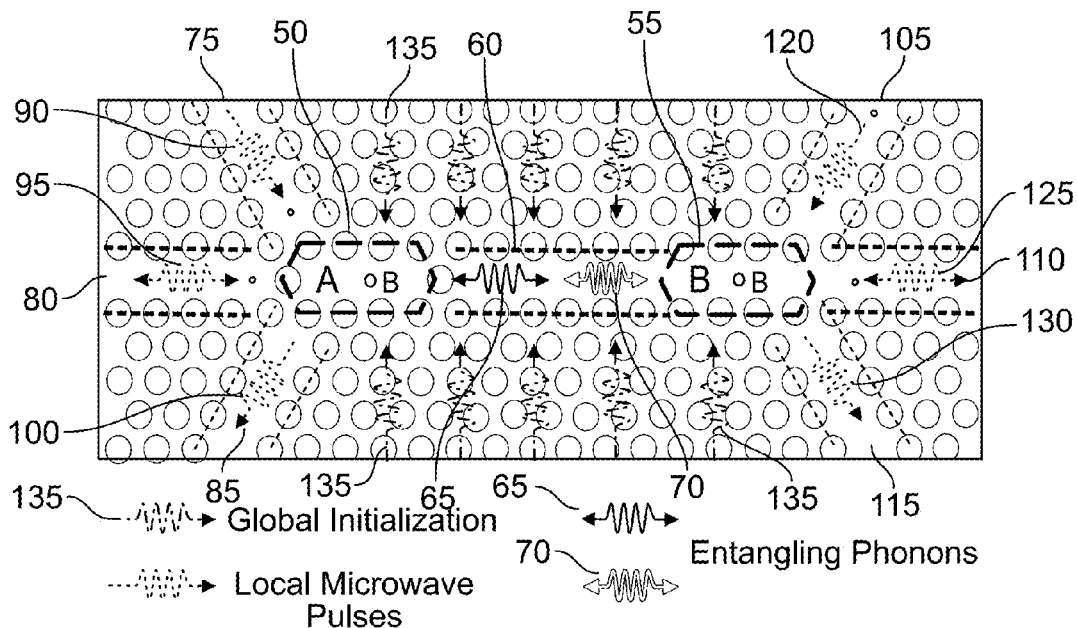
FIG. 3 is a schematic diagram, shown in plan view, of a two-qubit system according to certain principles described here.

Referring to FIG. 3, there will be seen a schematic diagram of a two-qubit system in which each of two phononic crystal cavities 50, 55 (respectively labeled A and B in the figure) contains a single acceptor boron atom. The cavities are both coupled to a PnC waveguide 60 in which entangling phonons 65, 70 (described below) can propagate. Cavity 50 is coupled to PnC waveguides 75, 80, 85, in which respective local "microwave" pulses 90, 95, 100 can propagate. Cavity 55 is coupled to PnC waveguides 105, 110, 115, in which respective local "microwave" pulses 120, 125, 130 can propagate. Also indicated in the figure are phononic global initialization pulses 135. The frequencies of these phonons lie outside the phononic band gap, so that they are supported by, and can propagate through, the lattice. By contrast, the local pulses have frequencies within the band gap and are transmitted only through waveguides.

It is important to note that the term "microwave" in this discussion refers to phonon frequencies. All of the atomic transitions to be described involve the absorption or emission of phonons.

We will now describe an example procedure for producing an entangled state between atoms A and B. Our description is best understood by referring concurrently to FIG. 3 and to FIG.

Figure 4:
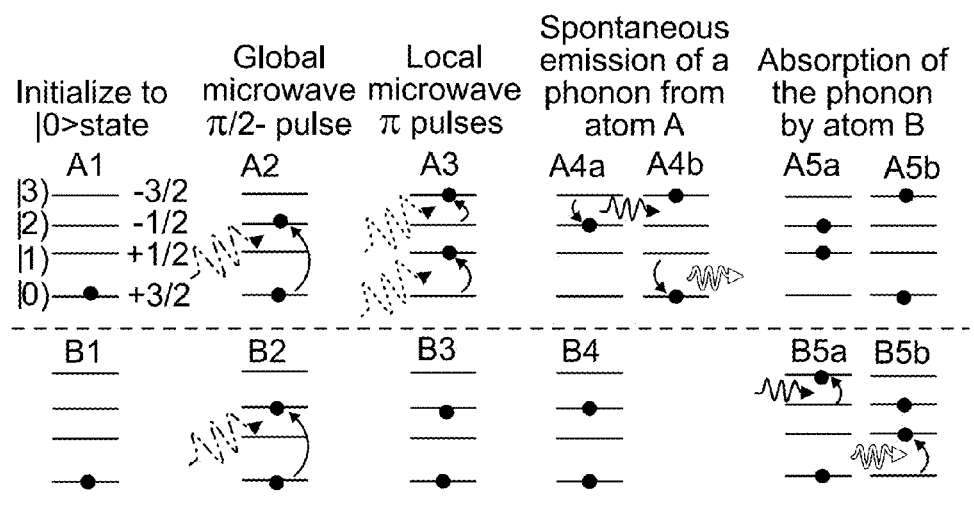
FIG. 4 is a series of frames that sequentially illustrate a method for producing an entangled state according to certain principles described here. Each frame contains an energy-level diagram corresponding to the pertinent states in the fine structure of two implanted boron atoms A and B. Sequential transitions among the energy levels are indicated in the respective frames.

(1) Initially, the system is cooled in a $^3$He cryostat. This forces the atoms to the $m_J=+3/2$ ground states shown as A1 and B1 in the first frame of FIG. 4. (2) A global microwave $\pi/2$ pulse 140 then excites atoms A and B to an equal superposition of the −1/2 and +3/2 states as indicated by A2 and B2 in the second frame of FIG. 4. (3) A local microwave pulse 90 applied to atom A renders it in an equal superposition of the −3/2 and +1/2 states as indicated by A3 in the third frame of FIG. 4. (4) Atom A then decays via path A4a or A4b, as indicated in the fourth frame of FIG. 4. This decay takes place by spontaneously emitting a phonon into waveguide 60 that is absorbed by the atom in cavity B. Atoms A and B are now in a non-separable entangled state.

In order from lowest to highest energy, we designate the +3/2, +1/2, −1/2, and −3/2 states by the following symbols, respectively: $|0\rangle$, $|1\rangle$, $|2\rangle$, $|3\rangle$. In that notation, Step (1) produces the two-atom state $|\Psi\rangle = |\Psi\rangle_a \otimes |\Psi\rangle_b = |0\rangle_a |0\rangle_b$. Step (2) produces $|\Psi\rangle = (1/2)(|0\rangle_a + |2\rangle_a) \otimes (|0\rangle_b + |2\rangle_b)$. Step (3) produces $|\Psi\rangle = (1/2)(|1\rangle_a + |3\rangle_a) \otimes (|0\rangle_b + |2\rangle_b)$.

The phonon emission by atom A in Step (4) produces:

$$|\Psi\rangle = (1/2)[(1/\sqrt{2})(|1\rangle_a + |2\rangle_a)|r\rangle_{ph} + (1/\sqrt{2})(|0\rangle_a + |3\rangle_a)|b\rangle_{ph}] \otimes (|0\rangle_b + |2\rangle_b).$$

Here, $|r\rangle_{ph}$ represents a "red" or slightly lower-energy phonon and $|b\rangle_{ph}$ represents a "blue" or slightly higher-energy phonon.

The phonon absorption by atom B in Step (4) produces:

$$|\Psi\rangle = (1/\sqrt{8})[(|1\rangle_a + |2\rangle_a)(|0\rangle_b |3\rangle_b) + (|0\rangle_a + |3\rangle_a)(|1\rangle_b + |2\rangle_b)].$$

A change of basis to new basis vectors $|x\rangle$ and $|y\rangle$ can transform the last expression, above, to a more easily recognized form of a maximally entangled state of two qubits:

$$|\Psi\rangle = (1/\sqrt{2}) \cdot [|y\rangle_a |x\rangle_b + |x\rangle_a |y\rangle_b].$$

Here, $x\rangle$ is a linear combination of $|0\rangle$ and $|3\rangle$, and $|y\rangle$ is a linear combination of $|1\rangle$ and $|2\rangle$, as given by:

$$|x\rangle = (1/\sqrt{2}) \cdot (|0\rangle + |3\rangle)$$

$$|y\rangle = (1/\sqrt{2}) \cdot (|1\rangle + |2\rangle).$$

Figure 5:
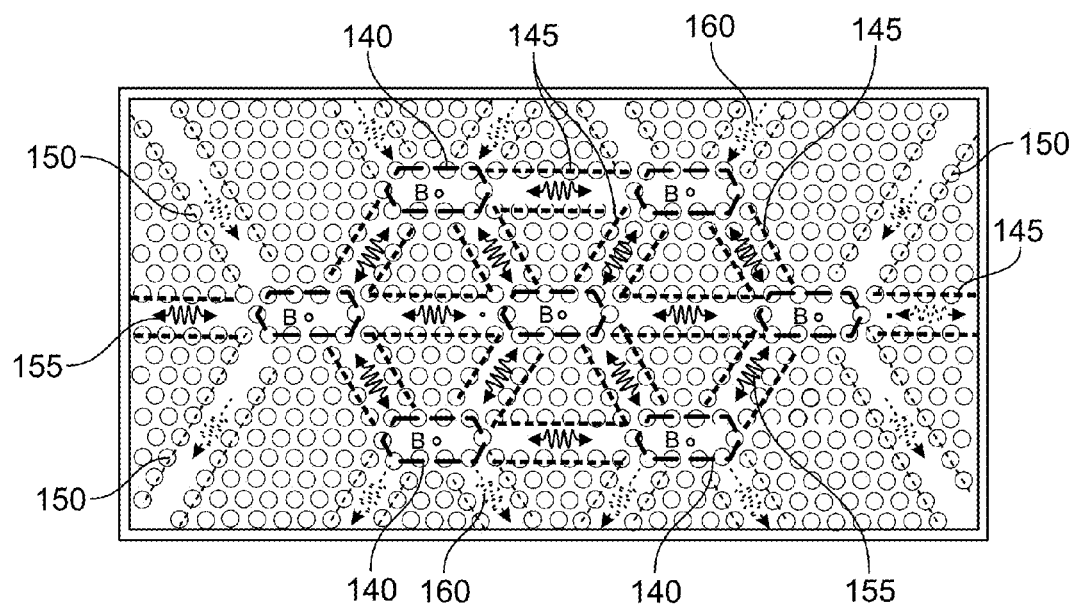
FIG. 5 is a schematic drawing, in plan view, of an example scaled-up architecture in which multiple phononic crystal (PnC) cavities are phononically coupled by waveguides.

An important feature of our PnC platform is that it can be scaled up to include larger numbers of resonantly coupled PnC cavities and waveguides. For example, FIG. 5 provides a schematic view in which a regular two-dimensional array of PnC-cavities 140 are resonantly coupled and interconnected by waveguides 145, 150. In the figure, entangling phonons 155 are notionally represented by wiggly arrows within waveguides in the center of the figure and entering and leaving at the right-hand and left-hand sides of the figure. Local microwave pulses 160 are notionally represented by the wiggly arrows within waveguides near the upper and lower borders of the figure.

In a platform such as the platform of FIG. 5, it is desirable to separate the cavities by enough distance to prevent interactions between them that would otherwise cause splitting of the cavity energy levels. Energy splitting is undesirable because it leads to undesirable inhomogeneities in the cavity population. Although we do not presently have a value for the lower limit on the inter-cavity separation (i.e., the entangling waveguide length), we currently envisage a separation of 100 μm, which is believed sufficient. This value imposes an upper limit of 127 possibly entangled qubits per squared centimeter. Of course greater areal densities will be achievable with shorter entangling waveguides.

Figure 6:
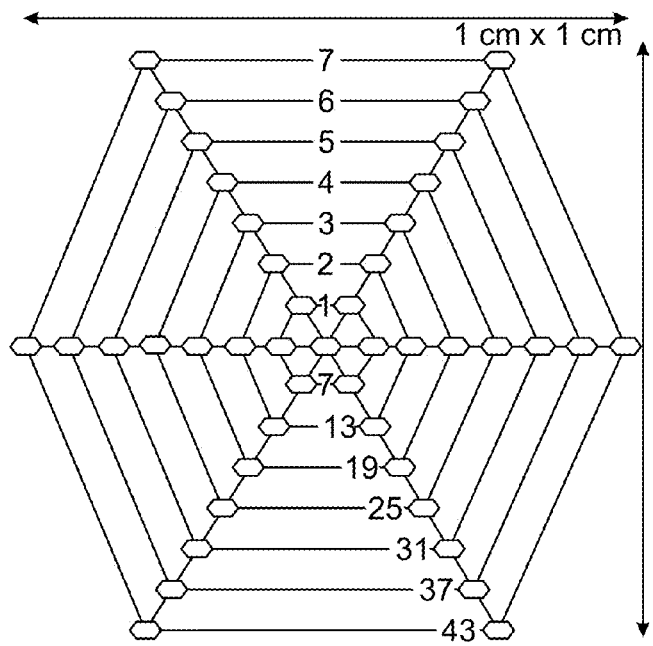
FIG. 6 is a geometrical construction illustrating the packing of coupled cavities within a PnC while maintaining a minimum separation between cavities.

FIG. 6 is a geometrical construction illustrating how 127 coupled qubits can be packed in a one-centimeter square with a minimum separation of 100 μm between cavities. The figure demonstrates that the packing is achievable with at least the number of qubits shown, using the hexagonal packing that is illustrated. Six rings are shown, numbered sequentially from 1 to 7. Populating each ring, in sequence, with six equally spaced qubits (and starting from one qubit at the center) yields, as shown, total counts of coupled qubits of 7, 13, 19, 25, 31, 37, and 43, respectively. Of course interstitial qubits can also be added to at least some rings, leading to even denser packing.

As is generally the case in devices quantum computing, the state of the entangled qubits can be interrogated in a process that is the reverse of the process of exciting the qubits. This can be done in our platform using global or local phononic interrogation signals.

It is important to understand that in the scheme of FIG. 5 there would be two different types of waveguides: the entangling waveguides 145 and the local microwave-pulse initialization waveguides 150. The optimal waveguide width is approximately one-half the acoustic wavelength at the pertinent phonon frequency. Accordingly, the dimensions of each type of waveguide should be appropriately scaled to the pertinent phonon frequency.

Since these are phononic (thus, mechanical) waveguides, each waveguide can be brought into resonance (corresponding to an on state) and out of resonance (corresponding to an off state) by simply touching it with a MEMS cantilever. This modulates the mechanical impedance of the waveguides and thus essentially brings them in and out of resonance with the cavities. It is significant that in implementations, the MEMS modulation (i.e. the electromechanical switching rate) can be in the megahertz range, which is well within the range of feasibility. By contrast, analogous photonic systems could be difficult to realize because of prohibitively high optical emission rates that might require terahertz modulation.

Figure 7:
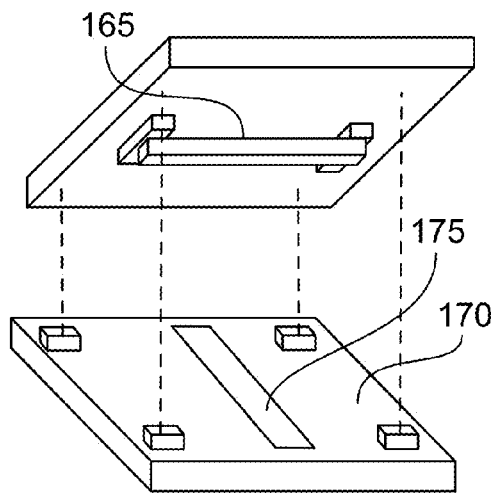
FIG. 7 is a schematic perspective view of an arrangement in which cantilevers are actuated to place selected waveguides in on or off states.

In an implementation as illustrated in the schematic perspective view of FIG. 7, the MEMS cantilever 165 is fabricated on a separate substrate from the phononic crystal 170 and waveguide 175, and the respective substrates are assembled face-to-face. (In the figure view, the cantilever is on the upper substrate and the phononic crystal is on the lower substrate.) The MEMS cantilever is actuated by any of various mechanisms, including for example electrostatic or piezoelectric actuation. In the case of piezoelectric actuation, an actuating voltage may be applied between the ends of the cantilever beam. In the case of electrostatic actuation, the actuation voltage may be applied between, e.g., the cantilever beam and the opposing phononic crystal substrate. In the assembled structure, the respective substrates may be separated by spacers 180 arranged, for example, at the corners of the substrates. The attachment of the substrates to each other may be according to any of various known assembly techniques such as flip-chip assembly.

Figure 8:
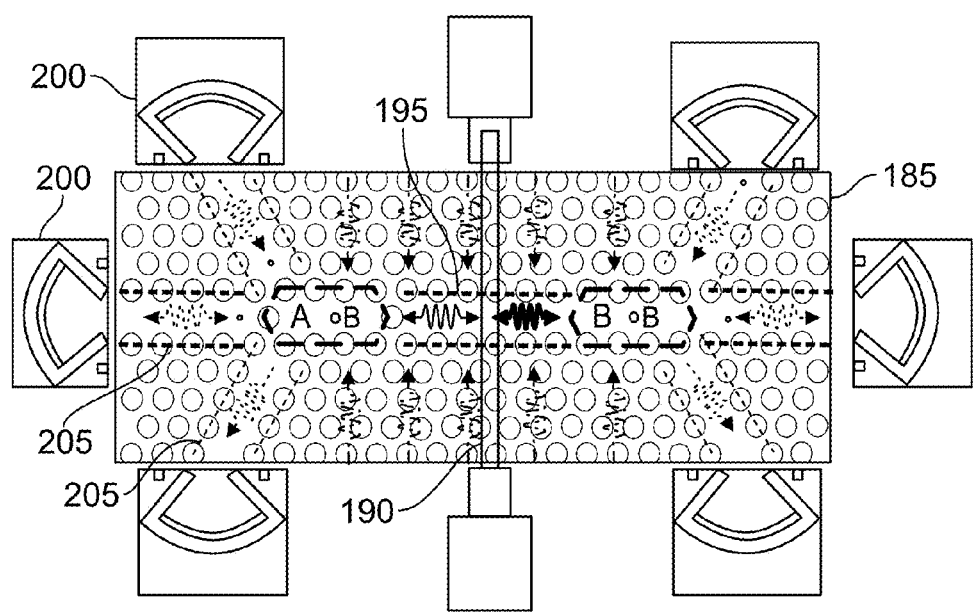
FIG. 8 provides a partially schematic plan view of an arrangement in which a phononic crystal is contacted from above by a MEMS cantilever beam.

FIG. 8 provides a partially schematic plan view in which the phononic crystal 185 is shown as being contacted from above by MEMS cantilever beam 190, which is positioned so as to reversibly contact waveguide 195. Also shown in the figure are focusing aluminum nitride acoustic transducers 200 for injecting the local microwave pulses into waveguides 205.

Design.

As explained above, each qubit is realized in the electronic states of a single acceptor atom. It should be noted in this regard that single-ion implantation techniques are well known. For example, implantation of single ions of phosphorus into silicon is described in T. Schenkel et al., "Solid state quantum computer development in silicon with single ion implantation," *J. Appl. Phys.*, 94 (2003) 7017 (hereinafter, "Schenkel 2003"). Schenkel 2003 describes the observation and characterization of implantation events using secondary ion detection and measurement. The entirety of Schenkel 2003 is hereby incorporated herein by reference.

SRIM ("the Stopping and Range of Ions in Matter") is a collection of software packages, available at srim.org, that calculate many features of the transport of ions in matter. We used a SRIM-2009 software package to estimate the placement straggle of a boron atom accelerated at 12 keV into a silicon substrate. The estimated straggle was found to be 50±22 nm for the depth, where 50 nm is the desired depth. The estimated lateral straggle was 23 nm. We believe that lateral positioning can be localized using a combination of beam spot size and masking using, e.g., a PMMA mask.

In our design efforts, we tried to optimize the dimensions of the phononic crystal cavity to accommodate these constraints with a sufficient error buffer, i.e. with a modal volume large enough to contain the straggle.

Figure 9:
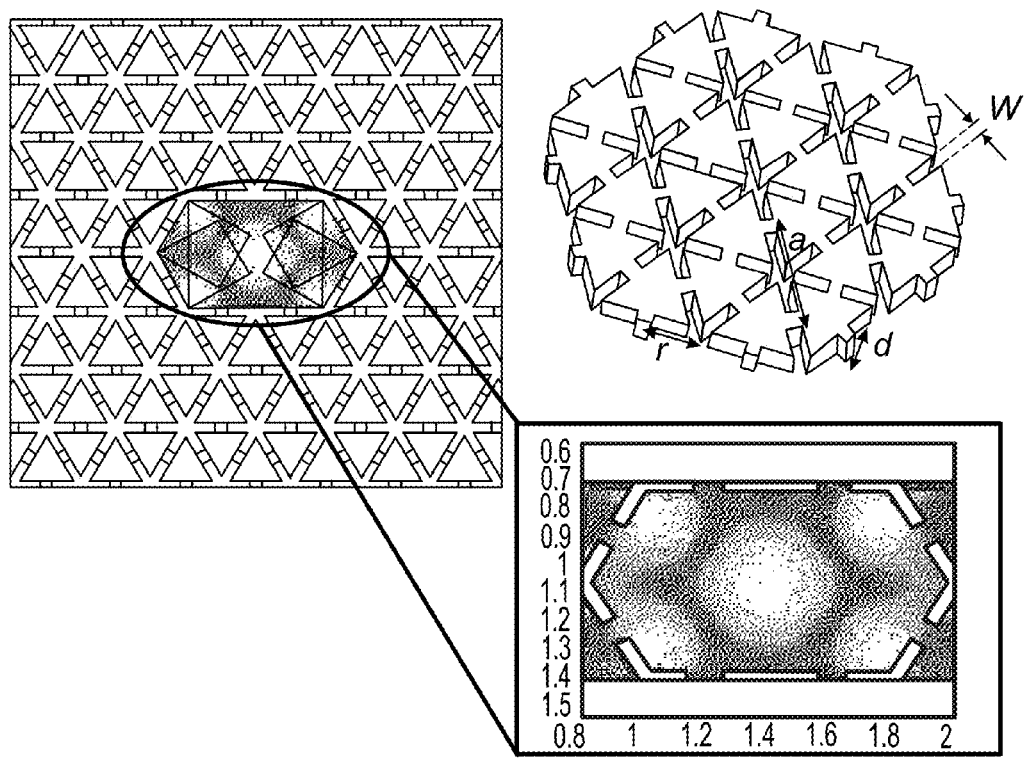
FIG. 9 provides, in the main view, a geometrical design of a representative phononic crystal. An inset indicates the geometrical design parameters and provides representative values for them. Another inset provides theoretical contours of the cavity mode.

FIG. 9 illustrates the design for a representative phononic crystal that was modeled. As shown, a silicon membrane of thickness d=160 nm is patterned as a close-packed array of equilateral triangles of lattice constant a=500 nm. The triangles are separated by narrow gaps bridged by radially extending arms of length w=75 nm. Such an arrangement may be viewed as a hole lattice of lattice constant a=500 nm, in which each hole is a six-armed star of radius r=200 nm and arm thickness w=75 nm.

Numerical simulations predict that for such a structure, the central hot spot in the cavity displacement profile is 500 nm in diameter and extends to a depth of 160 nm, i.e. through the silicon membrane. The loaded cavity Q is predicted to lie in the range 5000-10,000.

The lower-right-hand inset of the figure shows the contours of the predicted cavity mode, derived from numerical modeling. The upper-right-hand inset shows the geometrical design parameters of the structure.

Figure 10:
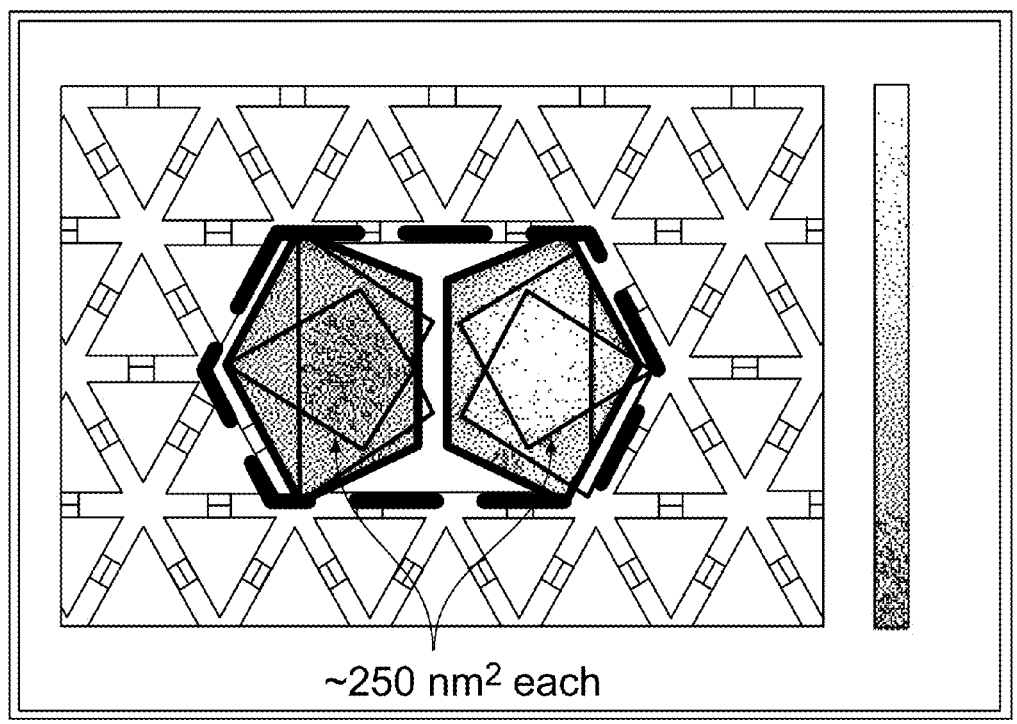
FIG. 10 provides a theoretical contour plot of the strain profile within the phononic cavity for the cavity mode of FIG. 9.

FIG. 10 provides a contour plot of the strain profile within the phononic cavity for the cavity mode of FIG. 9, derived from numerical modeling. It will be seen that the strain profile exhibits a maximum positive strain region (at the right-hand side of the cavity) and a maximum negative strain region (at the left-hand side of the cavity). It is preferable to situate the implanted ion in one of these two regions of maximum strain, rather than in the neutral region between them.

Figure 11:
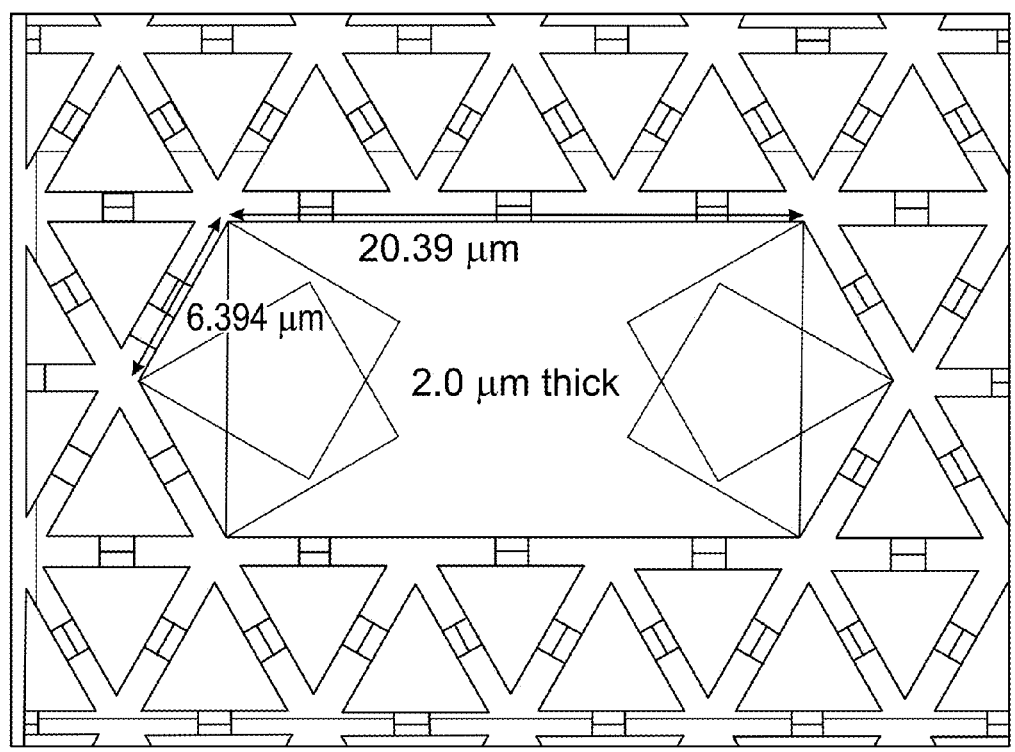
FIG. 11 is a detail of a geometrical design of a representative phononic crystal, indicating representative dimensions for a cavity.

FIG. 11 provides example dimensions for a phononic cavity. As seen, a row of holes is omitted, leading to a hexagonal region of the 2.0-nm-thick silicon membrane that has a long side length of 20.39 µm and a short side length of 6.394 µm.

Figure 12:
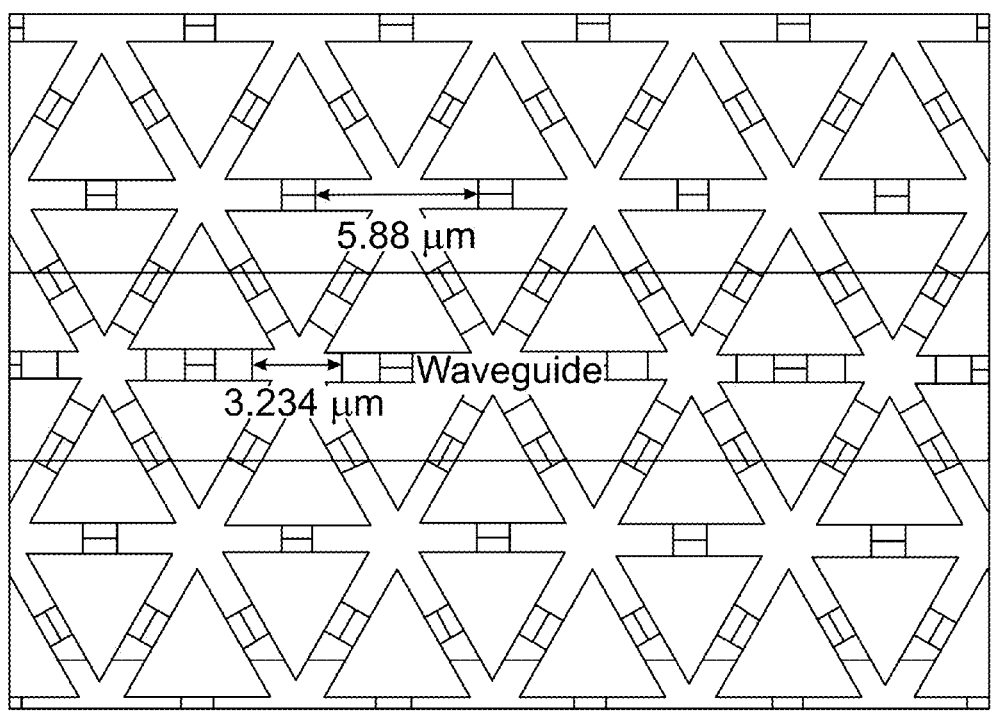
FIG. 12 is a detail of a geometrical design of a representative phononic crystal, indicating representative dimensions for a waveguide.

FIG. 12 provides example dimensions for a waveguide. As seen, the hole diameter in the waveguide region is reduced from 5.88 µm to 3.234 µm.

The waveguide depicted in FIG. 12 was designed, through an iterative process, to exhibit a phononic mode that coincides with the resonant mode of the cavities so that it can carry the phononic signals for entanglement. This can be understood in more detail with reference to FIG. 13, to which attention is now directed.

Figure 13:
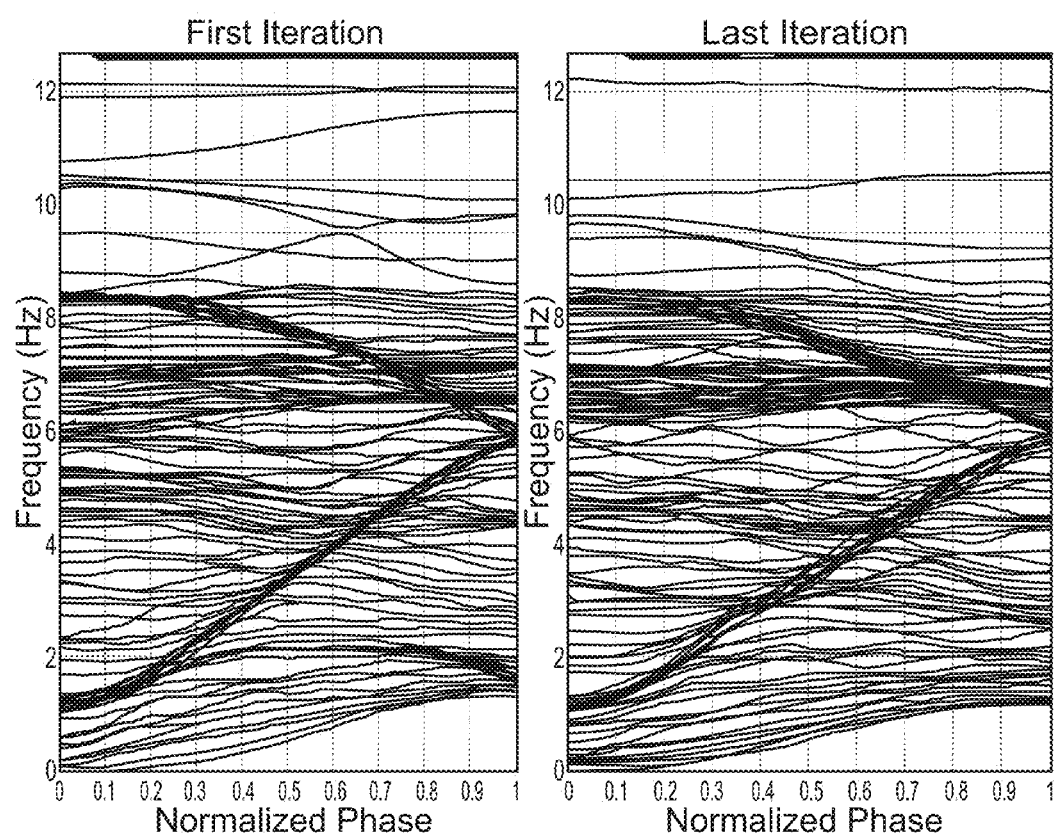
FIG. 13 provides a side-by-side view of a pair of dispersion plots for a phononic waveguide.

FIG. 13 provides, for comparison, a side-by-side pair of phonon dispersion plots for a phononic waveguide. In each graph, the phonon frequency is plotted against normalized phase (or equivalently, against normalized wavenumber). The left-hand graph represents the first of a series of design iterations, and the right-hand graph represents the last iteration. Each trace represents one waveguide mode. Additionally, an arrow superposed on each plot indicates the phononic cavity mode.

The waveguide design process was carried out iteratively with the objective of producing a single waveguide mode that intercepted the cavity resonance. The varied parameter was r/a, i.e., the radius of the six-armed stars, divided by the lattice constant.

The left-hand plot provides the results of the first iteration. The right-hand plot provides the results of the final iteration. It will be seen in the right-hand plot that there is one waveguide mode that intercepts the cavity resonance.

The strength of coupling between the waveguide and the cavity can be controlled by varying the geometrical distance between them. We conducted modeling studies in which the waveguide-to-cavity separation was varied over a range from about 400 nm to about 1600 nm. We found that over that range, the coupling varied from over-coupled, through critically coupled, to under-coupled, and the Q-factor varied from 55,100 in the over-coupled configuration to 58,500 in the most under-coupled configuration. Although a critically coupled configuration is acceptable, a slight amount of undercoupling is preferred, in order to assure that phonons can escape from the cavities for transmission.

Fabrication.

As noted above, an exemplary thickness for the silicon membrane in which the phononic crystal is defined is 160 nm. In implementations, such a structure is fabricated on a silicon substrate by etching a sacrificial layer so as to undercut and suspend an overlying layer of silicon.

Fabrication methods for silicon-based phononic crystals are well known in the art and need not be described here in detail. Several published descriptions of pertinent fabrication techniques are found in:

J. Li et al., "Ion-beam sculpting at nanometer length scales," *Nature* 412 (2001) 166-169;

R. H. Olsson et al., "Microfabricated VHF acoustic crystals and waveguides," *Sensors and Actuators A (Physical)*, vol. 145-146, pp. 87-93, July-August 2008;

P. E. Hopkins et al., "Reduction in the Thermal Conductivity of Singe Crystalline Silicon by Phononic Crystal Patterning," *Nanoletters* 11 (2011) 107-112;

D. F. Goettler et al., "Realization of a 33 GHz Phononic Crystal Fabricated in a Freestanding Membrane," *AIP Advances* 1, 041403, 2011;

Charles M Reinke et al., "*Phonon manipulation with phononic crystals*", Report No. SAND2012-0127 (2012), OSTI_ID=1039017;

Olsson, Roy H., III et al., "Research on micro-sized acoustic bandgap structures", Report No. SAND2010-0044 (2010), OSTI_ID=984095;

T. Schenkel et al., "Solid state quantum computer development in silicon with single ion implantation," *J. Appl. Phys.* 94 (2003) 7017;

Y. M. Soliman et al., "Phononic crystals operating in the gigahertz range with extremely wide band gaps," *Applied Physics Letters* 97 (2010) 193502-1-3;

D. M. Stein et al., "Feedback-controlled ion beam sculpting apparatus," *Rev. Sci. Inst.* 75 (2004) 900-905;

U.S. Pat. No. 7,836,566, "Microfabricated Bulk Wave Acoustic Bandgap Device," issued Nov. 23, 2010 to R. H. Olsson et al.; and U.S. Pat. No. 8,508,370, "Synthetic Thermoelectric Materials Comprising Phononic Crystals," issued Aug. 13, 2013 to I. F. El-Kady et al.

The entirety of each of the publications listed above is hereby incorporated herein by reference.

The interdigitated transducer (IDT) electrodes are fabricated on an aluminum nitride (AlN) film deposited on top of the silicon phononic crystal membrane and are aligned with their respective waveguide structures in the phononic crystal. Acoustic coupling between the transducers and the waveguides is achievable in this manner.

Preferred IDTs for use in the present context are designed for producing Gaussian Lamb-wave beams that can be efficiently coupled to small structures. One example of such a design is described in M. Eichenfield and R. H. Olsson III, "Design, fabrication, and measurement of RF IDTs for efficient coupling to wavelength-scale structures in thin piezoelectric films," 2013 *Joint UFFC, EFTF and PFM Symposium*, IEEE (2013), the entirety of which is hereby incorporated herein by reference.

One significant feature of our system is its tolerance to fabrication errors. An error in the phononic crystal fabrication could shift the cavity resonance off of a design value. (A typical design value is 5 GHz.) However, the bandwidth of the cavity will exceed the width of the atomic resonance (which is in the kilohertz to megahertz range) by about three orders of magnitude or more. Hence, such a fabrication error will not prevent the device from operating. It will only weaken the cavity-atom coupling and reduce the emission rate.

Figure 14:
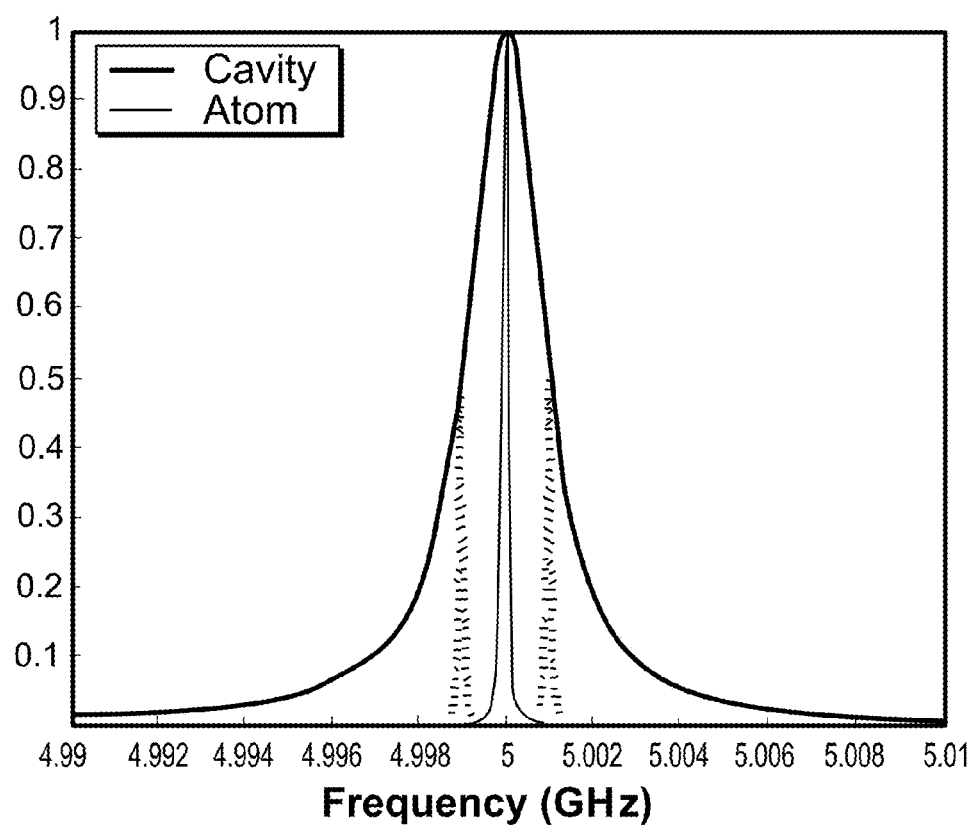
FIG. 14 provides the response spectrum of a resonant cavity, superimposed on the response spectrum of an implanted atom. Also shown in the figure are atomic response spectra (shown as broken lines) representing resonance mismatches of about +1 MHz and about −1 MHz.

FIG. 14 illustrates the effect of such a resonance mismatch. Seen in the figure are a spectrum illustrating the resonant frequency for the cavity (outer envelope) superposed on a spectrum illustrating the resonant frequency for the atom (inner envelope). It is evident in the figure that the atomic resonance is much narrower than the cavity resonance. Broken lines in the figure represent atomic spectra illustrative of resonance mismatches of about +1 MHz and about −1 MHz. It will be seen that in both cases, the atomic resonance still falls well within the cavity bandwidth.

The invention claimed is:

1. A quantum device, comprising:
a phononic crystal defined on a semiconductor substrate;
a plurality of phononic cavities defined in the phononic crystal, wherein each phononic cavity contains an implanted acceptor atom; and
a plurality of phononic waveguides defined in the phononic crystal, wherein each waveguide is coupled to at least one phononic cavity;

wherein at least some phononic waveguides are arranged to provide coupling between phononic cavities and ultrasonic transducers; and wherein at least some phononic waveguides are arranged to provide coupling between different phononic cavities.

2. The quantum device of claim 1, further comprising at least one ultrasonic transducer acoustically coupled to one or more of the phononic waveguides.

3. The quantum device of claim 2, wherein at least one said ultrasonic transducer is an aluminum nitride interdigitated transducer.

4. The quantum device of claim 1, further comprising a plurality of MEMS beams, each of which is configured to controllably and reversibly make mechanical contact with a respective one of the phononic waveguides.

5. The quantum device of claim 1, wherein the semiconductor substrate is a suspended silicon membrane.

6. The quantum device of claim 5, wherein the acceptor atoms are boron atoms.

7. The quantum device of claim 1, wherein:

at least some of the phononic waveguides arranged to provide coupling between phononic cavities and ultrasonic transducers are tuned to a local initialization frequency; and at least some of the phononic waveguides arranged to provide coupling between different phononic cavities are tuned to an entanglement frequency that is unequal to the local initialization frequency.

8. The quantum device of claim 7, further comprising:

at least one ultrasonic transducer acoustically coupled to one or more phononic waveguides tuned to a local initialization frequency; and at least one ultrasonic transducer acoustically coupled to the semiconductor substrate and tuned to a global initialization frequency that propagates in the phononic crystal without waveguide confinement.

9. The quantum device of claim 1, wherein the phononic crystal is defined by a regular two-dimensional lattice of holes in the semiconductor substrate, the phononic cavities are defined by the absence of holes in cavity regions, and the phononic waveguides are defined by a change in hole dimensions in waveguide regions.

10. The quantum device of claim 1, wherein:

the phononic cavities have a resonant frequency; and the waveguides arranged to provide coupling between different phononic cavities are configured to have only one mode capable of oscillating at the cavity resonant frequency.

* * * * *